United States Patent [19]

Numata

[11] 4,389,565
[45] Jun. 21, 1983

[54] AUTOMATIC FOCUS CONTROLLING DEVICE

[75] Inventor: Saburo Numata, Urawa, Japan

[73] Assignee: Fuji Photo Optical Co., Ltd., Japan

[21] Appl. No.: 238,747

[22] Filed: Feb. 27, 1981

[30] Foreign Application Priority Data

Feb. 29, 1980 [JP] Japan .................. 55/24772

[51] Int. Cl.$^3$ .............................................. G01J 1/20
[52] U.S. Cl. .................................... 250/201; 250/227
[58] Field of Search .......................... 250/201, 227; 350/96.26; 354/25 R

[56] References Cited

U.S. PATENT DOCUMENTS 4,340,811 7/1982 Yamashita et al. ................. 250/201

Primary Examiner—David C. Nelms
Assistant Examiner—Darwin R. Hostetter

[57] ABSTRACT

In an optical instrument such as a photographic camera or an endoscope, the focus of an image of the object to be observed or photographed is automatically controlled based on the distance automatically measured. The distance of the object is automatically measured by use of a light source for illuminating the object, a photodetector, an image focusing optical system for focusing the image of the object on the photodetector, and an electric circuitry connected with the photodetector. The intensity of the illumination is periodically changed and the light reflected by the illuminated object received by the photodetector is measured. When the level of the output of the photodetector becomes equal to a predetermined level, a signal is generated to indicate that the brightness of the illuminated object has reached a predetermined level. Since the light intensity of the illumination at this point corresponds to the distance of the object, the distance is thus measured. According to the measured distance, a focusing lens is driven to automatically obtain a focused image.

8 Claims, 3 Drawing Figures

AUTOMATIC FOCUS CONTROLLING DEVICE

BACKGROUND OF THE INVENTION

1. Field of the Invention

This invention relates to an automatic focus controlling device for an optical instrument such as a photographic camera or an endoscope, and more particularly to a device for automatically detecting the distance of an object and controlling focus based on the detected distance which is adaptable to any existing optical instrument.

2. Description of the Prior Art

In an optical instrument having an objective such as a photographic camera or an endoscope, it is desirable to automatically control the focus of the image of the object to be viewed or photographed. There have been developed and suggested various kinds of focus detecting or adjusting devices for photographic cameras. They are, however, provided with a special and complex focus detecting means in addition to the conventional structure of the optical instrument.

Particularly in an endoscope, it is undesirable to provide an additional focus detecting device at the head of the flexible optical fiber tube thereof because the head is desired to be as thin as possible to minimize the pain to the patient.

In an endoscope, it has been known to project an image of a pinhole onto the object to be observed and detect the image on the object to adjust the focus as disclosed in Japanese Unexamined Patent Publication No. 12193/1978 filed July 20, 1976. In this focus adjusting system using a pinhole image, the focus adjustment must be conducted before the photographing operation and accordingly the projection of the pinhole is turned off when photographing. Further, the fiber tube is partly used for projecting the pinhole image and not fully used for viewing the object. Thus, the structure and the operation of the endoscope are complex due to the additional optical system and operation required for projecting and viewing the pinhole image and also adjusting focus.

Further, it has been known in the art to use a spatial frequency filter to detect the focus. However, since the contrast of the image within the body cavities is very low, the accuracy of the focus detection by use of the spatial frequency filter cannot be made so high.

SUMMARY OF THE INVENTION

The primary object of the present invention is to provide an automatic focus controlling device for use in an optical instrument such as a photographic camera or an endoscope which has a very simple structure and can very easily be operated.

Another object of the present invention is to provide an automatic focus controlling device particularly useful in an endoscope which does not require any additional mechanism or optical means for focus control in addition to the conventional endoscope.

The focus controlling device in accordance with the present invention is characterized in that the distance of the object is automatically measured by use of an electric circuitry connected with a light source for illuminating the object and a photodetector for receiving light from the illuminated object. The photodetector is provided to receive the light from the illuminated object by way of an optical fiber bundle in case of an endoscope. In case of a photographic camera, the photodetector receives light directly from the illuminated object. In case of the photographic camera, a light source for detecting focus such as an infrared ray source is used for illuminating the object. The present invention is based on a concept that the reflection coefficient of the object is statistically constant around 20 to 30% and the degree of diffusion of the light emitted by the light source is constant. In the device of this invention, the intensity of the illumination is varied continuously and the point where the amount of light received by the photodetector reaches a predetermined value is detected. Since that point corresponds to the distance of the object in view of the constant reflection coefficient and the constant degree of diffusion of the light, the distance of the object can be detected thereby. According to the detected distance, the focus adjustment of the taking lens or objective of the optical instrument is conducted.

In case of an endoscope, the object is illuminated only by the illuminating light source provided on the endoscope, and accordingly the focus detection is made only by use of the light from the light source. In case of the photographic camera, the light used for detecting focus should be distinguished from the existing light illuminating the object such as the sunlight or artificial light. Therefore, as the light of illumination to be used for detecting focus is used in infrared ray for instance.

DESCRIPTION OF THE PREFERRED EMBODIMENT

Now the present invention will be described in detail with reference to the accompanying drawings.

Figure 1:
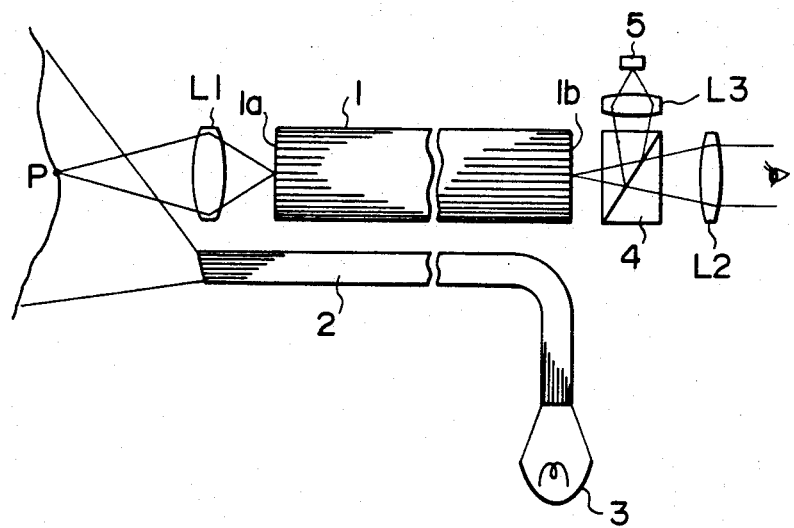
FIG. 1 is a schematic side view showing the whole optical system of an embodiment of the focus controlling device adapted to an endoscope in accordance with the present invention.

Referring to FIG. 1 which shows the optical system of an endoscope provided with the focus controlling device in accordance with the present invention, a light source 3 illuminates an object P by way of a light transmitting fiber tube 2 for illumination. The light transmitting fiber tube 2 for illumination is provided in parallel with an image transmitting fiber tube 1. In front of the image transmitting fiber tube 1 is provided an objective L1 to focus an image of the object P on the entrance face 1a thereof. Between the exit face 1b thereof and an eyepiece L2 is located a semi-transparent mirror prism 4 which partly transmits light from the exit face 1b to the eyepiece L2 and partly reflects light from the exit face 1b toward a focusing lens L3 to focus an image of the object P on a photodetector 5. The focusing lens L3 focuses the image of the object P appearing on the exit face 1b onto the photodetector 5.

Since an endoscope is usually provided with an illuminating light source like the above mentioned light source 3, there is required no additional element in this respect. Only the photodetector 5 and the semi-transparent mirror prism 4 are additionally provided. However, these elements are simply located between the exit face 1b of the image transmitting fiber tube 1 and the eyepiece L2. Therefore, there is no particular optical instrument affecting the thickness of the head or flexible fiber tube inserted into a body cavity. Further, as is well known in the art, some endoscopes are provided with a light measuring device for controlling photographic exposure consisting of a semi-transparent mirror prism, a photodetector and a focusing lens just as those employed in the embodiment as shown in FIG. 1. Therefore, in such an endoscope, there is required no optical element added thereto.

Figure 3:
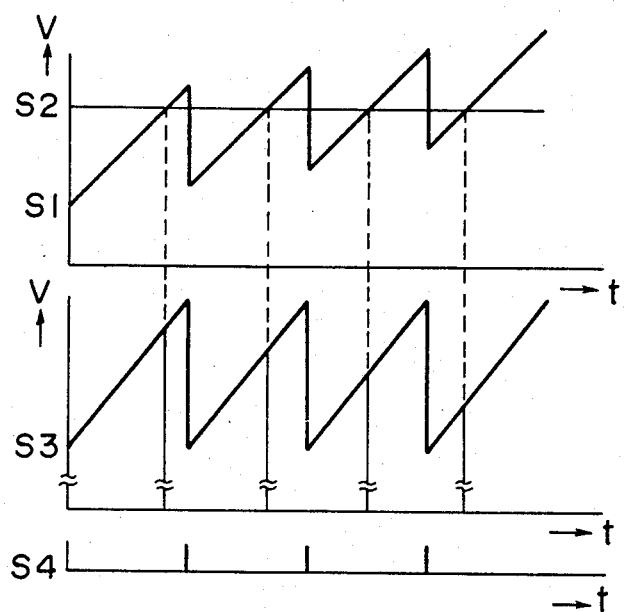
FIG. 3 is a time chart showing the waveform of signals handled in the circuitry shown in FIG. 2.
Figure 2:
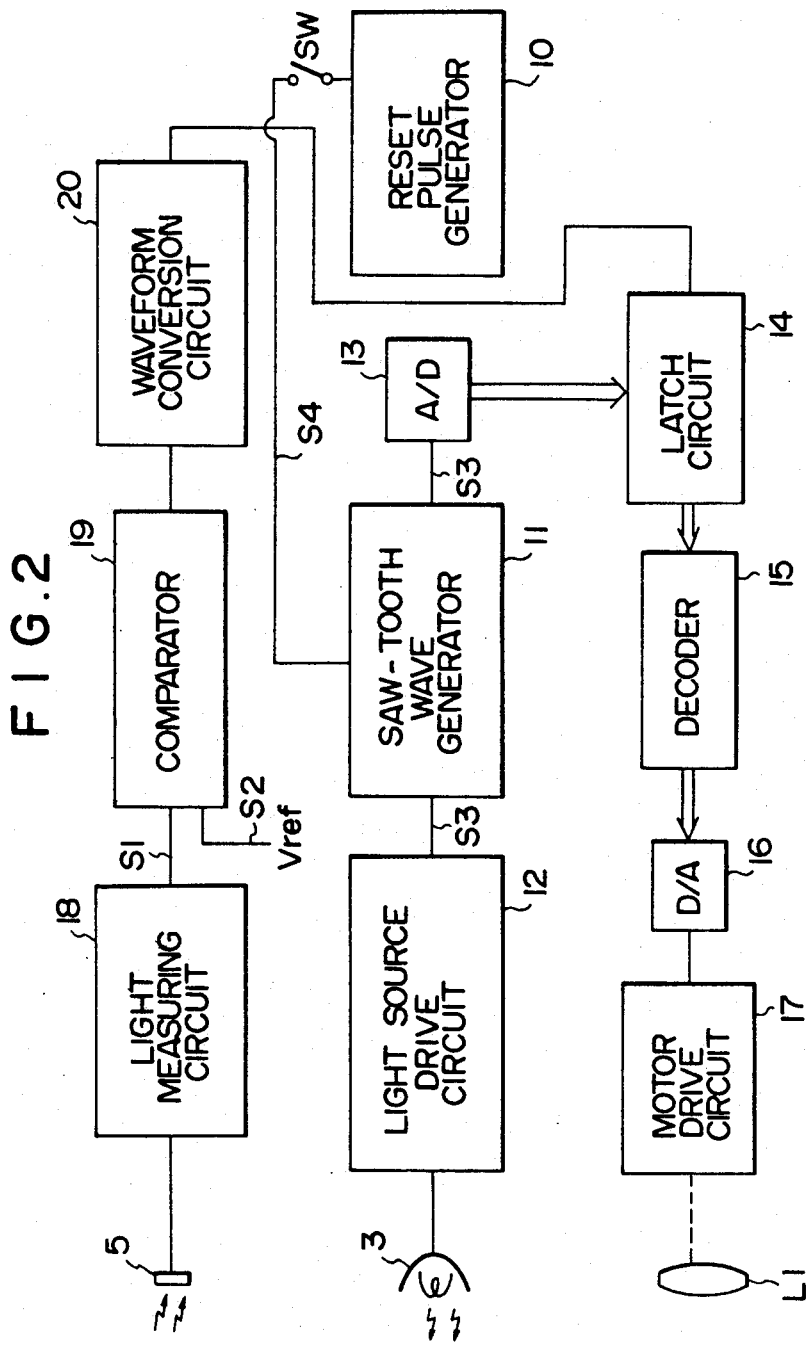
FIG. 2 is a block diagram of an electric circuitry for detecting focus in accordance with an embodiment of the present invention.

Referring now to FIGS. 2 and 3, an electric circuitry for detecting the distance and controlling the focus will be described in detail. In FIG. 2, all the elements equivalent to those shown in FIG. 1 are designated with the same reference numerals. A reset pulse generator 10 generates a series of pulses by way of a switch SW and causes a saw-tooth wave generator 11 to generate a saw-tooth voltage changing between a low voltage and a high voltage repeatedly. The changing voltage drives a light source drive circuit 12 to give a repeatedly changing voltage to a lamp 3. The period of the voltage change thus obtained is desired to be about 0.05 second or less in order to prevent an after image effect sensed by the observer. Thus, the intensity of the light emitted by the lamp 3 is periodically changed without being sensed by the observer of the endoscope.

The image of the object P illuminated by the lamp 3 is focused on the photodetector 5 by way of the objective L1, the image transmitting fiber tube 1, the semi-transparent mirror prism 4 and the focusing lens L3. The output of the light measuring circuit 18 connected with the photodetector 5 is, therefore, changed repeatedly between a low voltage and a high voltage according to the output of the drive circuit 12.

The output S1 of the photodetector 5 obtained through the light measuring circuit 18 is compared with a reference voltage L2 at a comparator 19. When the output S1 of the light measuring circuit 18 has reached the level of the reference voltage S2, the output of the comparator 19 is inverted. The inverted output of the comparator 19 is converted to a pulse by a waveform conversion circuit 20, which in turn is used as a latch pulse for a latch circuit 14. The latch circuit 14 is connected with an A/D converter 13 which converts the analog signal S3 of said saw-tooth wave generator 11 to a digital signal, and receives the digital signal to latch the digital amount at the time when the output of the comparator 19 is inverted. The latched digital amount is input into a decoder 15 consisting of a memory like a ROM. The digital amount thus input into the decoder 15 is converted to another digital amount corresponding to the distance of the object according to a predetermined information regarding the relationship between the output of the light measuring circuit 18 indicative of the brightness of the object illuminated by the light source 3 and the distance of the object calculated in view of the statistically constant reflection coefficient of the object and the constant degree of diffusion of the light emitted by the light source 3. The brightness B of the object P can be represented by a formula $$B = kI/Kr^2$$

where I is the intensity of the light source 3, K is the degree of diffusion, r is the distance of the object P from the entrance face 1a of the image transmitting fiber tube 1, and k is a constant depending upon the reflection coefficient of the object.

The digital amount thus obtained by the decoder 15 is then converted to an analog amount by an A/D converter 16. The output of the A/D converter 16 is connected to a motor drive circuit 17 to drive a motor to move the objective L1 to automatically focus the image of the object P.

Thus, the focus of the image observed or photographed is automatically controlled by automatically detecting the distance of the object.

The pulse generator 10 gives the pulses continuously to the saw-tooth wave generator 11 by way of the reset switch SW. The reset switch SW can be properly turned off to stop unnecessary focus detection or control to prevent of loss of power.

The light source 3 may be of a combination of a visible light source and an infrared ray source so that only the infrared ray may be taken out by the semi-transparent mirror prism 4 and the visible light may be fully used for observation or photographing.

As described hereinabove, the focus controlling device in accordance with the present invention can be not only adapted to an endoscope but also adapted to a photographic camera or other optical instrument such as a television camera or any kind of viewing device having an objective.

I claim:

1. A device for automatically controlling focus adapted to an endoscope comprising an image transmitting fiber tube, an objective for focusing an image of an object to be observed or photographed on an entrance end face of the image transmitting fiber tube, an eyepiece for enlarging and viewing the image appearing at an exit end face of the image transmitting fiber tube, a light source for illuminating the object, a flexible light transmitting fiber tube for transmitting light from said light source to the object, and means for measuring the brightness of the object illuminated by said light source wherein the improvement comprises means for periodically changing the intensity of the light source, means for comparing the output of said brightness measuring means with a predetermined value and giving an output signal when the output of the measuring means has become equal to the predetermined value, means connected with said comparing means to receive said output signal for determining the distance of the object based on the intensity of the light source when the output signal is received thereby, and means for axially moving said objective to control focus according to the determined distance.

2. A device as defined in claim 1 wherein the period of the periodical change of the intensity is 0.05 seconds or less.

3. A device as defined in claim 1 wherein said light source is an infrared ray source.

4. A device for automatically detecting the distance of an object from an endoscope comprising an image transmitting fiber tube, an objective for focusing an image of an object to be observed or photographed on an entrance end face of the image transmitting fiber tube, an eyepiece for enlarging and viewing the image appearing at and exit end face of the image transmitting fiber tube, a light source for illuminating the object, a flexible light transmitting fiber tube for transmitting light from said light source to the object, and means for measuring the brightness of the object illuminated by said light source wherein the improvement comprises means for periodically changing the intensity of the light source, means for comparing the output of said brightness measuring means with a predetermined value and giving an output signal when the output of the measuring means has become equal to the predetermined value, and means connected with said comparing means to receive said output signal for determining the distance of the object based on the intensity of the light source when the output signal is received thereby.

5. A device for automatically detecting the distance of an object of an optical instrument comprising a light source for illuminating the object, means for measuring the brightness of the object illuminated by the light source, means for periodically changing the intensity of the light emitted by the light source, means for comparing the output of the brightness measuring means with a predetermined value and generating an output signal when the output of the measuring means has become equal to the predetermined value, and means connected with the comparing means to receive said output signal for determining the distance of the object based on the intensity of the light when the output signal is received thereby.

6. A device for automatically controlling focus of an image of an object of an optical instrument comprising a light source for illuminating the object, means for measuring the brightness of the object illuminated by the light source, means for periodically changing the intensity of the light emitted by the light source, means for comparing the output of the brightness measuring means with a predetermined value and generating an output signal when the output of the measuring means has become equal to the predetermined value, means connected with the comparing means to receive said output signal for determining the distance of the object based on the intensity of the light when the output signal is received thereby, and means for axially moving said objective to control focus according to the determined distance.

7. A device as defined in claim 5 or 6 wherein said light source is an infrared ray source.

8. A device as defined in claim 5 or 6 wherein the period of the periodical change of the intensity is 0.05 seconds or less.

* * * * *